United States Patent [19]

Nakajima et al.

[11] Patent Number: 4,990,511

[45] Date of Patent: Feb. 5, 1991

[54] AMIDE COMPOUNDS, THEIR PRODUCTION AND USE

[75] Inventors: Terumi Nakajima; Koichi Shudo, both of Tokyo; Giichi Goto, Toyono, all of Japan

[73] Assignee: Takeda Chemical Industries, Ltd., Osaka, Japan

[21] Appl. No.: 388,676

[22] Filed: Aug. 2, 1989

[30] Foreign Application Priority Data

Aug. 3, 1988 [JP] Japan .................................. 63-194246

[51] Int. Cl.$^5$ ................. A61K 31/495; A61K 31/445; A61K 31/535; C07D 295/10
[52] U.S. Cl. ............................ 514/255; 514/183; 514/212; 514/218; 514/238.8; 514/317; 514/330; 514/331; 514/365; 514/374; 514/385; 514/399; 514/423; 514/427; 514/428; 514/613; 514/615; 514/616; 514/617; 540/450; 540/607; 540/609; 540/610; 544/162; 544/168; 544/170; 544/390
[58] Field of Search .............. 544/390, 391, 400, 162, 544/168, 170; 546/226, 236, 225, 233; 564/139, 157, 155; 514/255, 317, 330, 616, 617, 183, 212, 218, 238.8, 255, 331, 365, 374, 385, 399, 423, 427, 428; 540/450, 607, 609, 610; 548/215, 341, 347, 378

[56] References Cited

U.S. PATENT DOCUMENTS

| | | | |
|---|---|---|---|
| 3,272,861 | 9/1966 | Riggs et al. | 546/298 |
| 3,988,363 | 10/1976 | Spirack et al. | 544/387 |
| 4,559,349 | 12/1985 | Storni | 514/318 |

FOREIGN PATENT DOCUMENTS

| | | |
|---|---|---|
| 0097096 | 12/1983 | European Pat. Off. . |
| 0156540 | 10/1985 | European Pat. Off. . |
| 0192431 | 8/1986 | European Pat. Off. . |
| 0311517 | 4/1989 | European Pat. Off. . |
| 862721 | 3/1961 | United Kingdom . |

OTHER PUBLICATIONS

Oediger et al., CA 72-21525b (1970).
Szolcsanyi et al., CA 84-116373n (1976).
Fujii et al., CA 107-197815b (1987).
Simon et al., CA 108-111956j (1988).
Wistrand et al., CA 108-150247y (1988).
Yuichi Hashimoto et al., "Synthesis of Spider Toxin (JSTX-3) and its Analogs", Tetrahedron Letters, vol. 28, No. 30, pp. 3511-3514, 1987.
S. A. Minasyan et al., "Phenolic Acid Derivatives", Chemical Abstracts, vol. 106, No. 5, Feb. 2, 1987.

*Primary Examiner*—Cecilia Shen
*Attorney, Agent, or Firm*—Wegner, Cantor, Mueller & Player

[57] ABSTRACT

Amide compounds having glutamate receptor-inhibiting activity and having the formula:

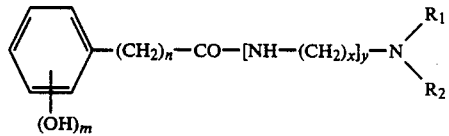

(wherein $R_1$ and $R_2$ each is hydrogen atom, an alkyl group or an acyl group, or

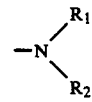

is a cyclic amino group, m is an integer of 1 to 3, n is an integer of 0 to 4, x is an integer of 2 to 6 and y is an integer of 0 to 3) or salts thereof, are provided. The compounds are useful as a medicine for therapy or/and prevention of sequelae of cerebral apoplexy in warm-blooded animals.

8 Claims, No Drawings

AMIDE COMPOUNDS, THEIR PRODUCTION AND USE

The present invention relates to a novel amide compound having a glutamate receptor-inhibiting activity and salts thereof.

Chemical substances in spiders which paralyze the nerve of anthropodes such as insects have been isolated and their structures have been elucidated to some extent. It has been confirmed that the nerve paralyzing action of those substances is due to glutamate receptor-inhibiting action. For instance, Proceedings of the Japan Academy, 62, Ser. B, 359 (1986) discloses $N^1$-(2,4-dihydroxyphenyl- acetylasparaginyl)-$N^5$-(arginyl-cadaverino-$\beta$-alanyl) cadaverin and the like and Chemical Abstracts, 105, 186106d (1986) discloses (2,4-dihydroxyphenylacetylasparaginyl)-polyamine-(arginyl) wherein the polyamine is $-NH(CH_2)_3NH(CH_2)_3NH(CH_2)_5NH-$.

Problems come up with respect to what is the essence of the action of the glutamate receptor-inhibiting substances including the above chemical substances and what chemical modification is possible.

The inventors synthesized compounds having a part of the structure of corresponding chemical substances and also the above chemical substances which were chemically modified and studied their glutamate receptor-inhibiting action to find whether the glutamate receptor-inhibiting action is developed by bonding a certain group to the partial structure of the above chemical substances. As the result of further investigation, the present invention has been accomplished.

That is, the compound of the present invention is a compound represented by the formula:

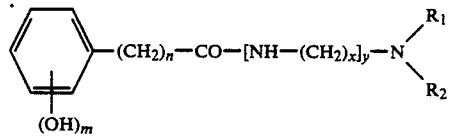

(wherein $R_1$ and $R_2$ each is hydrogen atom, an alkyl group or an acyl group, or

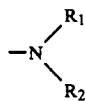

is a cyclic amino group, m is an integer of 1 to 3, n is an integer of 0 to 4, x is an integer of 2 to 6 and y is an integer of 0 to 3), or a salt thereof (abbreviated compound I hereinafter).

In the compound I, $R_1$ and $R_2$ each is hydrogen atom, an alkyl group or an acyl group. The alkyl group and the acyl group may have substituents. The alkyl group herein represents a lower alkyl group, preferably an alkyl group having 1 to 6 carbon atoms such as methyl, ethyl, propyl, butyl, etc. Substituents in the alkyl group include halogen, a hydroxyl group, an amino group and an oxo group. The acyl group includes a lower alkanoyl group (e.g. acetyl, propionyl group, etc.), an arylcarbonyl group (e.g. benzoyl), an aralkylcarbonyl group (e.g. phenylacetyl, phenylpropionyl, etc.). Substituents of the acyl group include halogen, a hydroxyl group, an amino group, an oxo group, etc. $R_1$ and $R_2$ in the

may combine to form a cyclic amino group expressed in

$-NR.$

The cyclic amino group represents a group formed by elimination of the hydrogen atom from HN in the cyclic amine represented by

HNR.

The cyclic amines represented by

HNR are preferably those with a 5- to 24-membered ring, preferably 5- or 6-membered ring. The number of nitrogen atoms constituting the ring is normally 1 to 8, preferably 1 to 6. Ring-constituting atoms other than nitrogen atom may be oxygen atom and sulfur atom in addition to carbon atoms. Further, the ring may contain a double bond.

As the cyclic amines represented by

HNR, mention may be made of, for example, pyrrole, pyrrolidine, imidazole, imidazolidine, pyrazole, oxazolidine, thiazolidine, piperidine, piperazine, morpholine, 1H-azepine, hexahydroazepine, hexahydrodiazepine (e.g., 1,4-), azacyclooctane, diazacyclooctane (e.g., 1,5-), triazacyclononane (e.g., 1,4,7-), tetraazacyclododecane (e.g., 1,4,7,10-), tetraazacyclotetradecane (e.g., 1,4,8,11-), tetraazacyclohexadecane (e.g., 1,5,9,13-) and hexaazacyclooctadecane (e.g., 1,4,7,10,13,16). The nitrogen atoms and/or carbon atom which constitute the R portion of the cyclic amine

HNR may have substituents. Substituents which bonds to a nitrogen atom constituting the R portion includes, for example, a lower alkyl group such as methyl, ethyl, propyl or butyl, an aryl group such as a phenyl group, an aralkyl group such as benzyl or benzhydryl, and an acyl group such as acetyl, propionyl, benzoyl, phenylacetyl, or phenylpropionyl. The substituent which bonds to the carbon atom in the R portion includes, for example, a lower alkyl group such as methyl, ethyl, propyl or butyl, an acyl group such as acetyl, propionyl, benzoyl, phenylacetyl, or phenylpropionyl, a lower alkylidene group such as methylene or ethylidene, an oxo group and a thioxo group. These substituents may combine to form a condensed ring. Such condensed cyclic amines include, for example, indole, 1H-indazole, purine, indoline, 1H-benzotriazole, phenoxazin, phenothiazine and carbazole.

The group

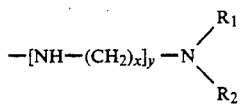

in the compound I indicates

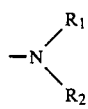

when y is 0,

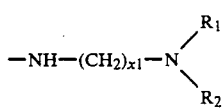

when y is 1,

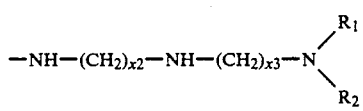

when y is 2, and

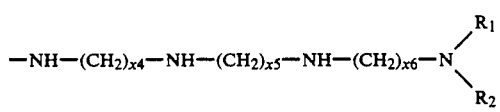

when y is 3, individually. Herein, x1–x6 each is an integer of 2 to 6, as in x.

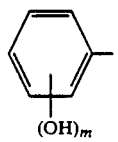

in the compound I indicates that 1 to 3 hydroxyl groups attach to any of the 2, 3, 4, 5 and 6 positions of the benzene ring. Examples are 2-dihydroxyphenyl, 3-hydroxyphenyl, 4-hydroxyphenyl, 2,4-dihydroxyphenyl, 3,4-dihydroxyphenyl and 2,4,5-trihydroxyphenyl. 2,4-dihydroxyphenyl is the most preferable.

In the compound I, n represents an integer of 0 to 4. In the case of n=0, the phenyl group directly bonds to the carbonyl group. n is preferably 1 to 3. The compound I may be a salt with inorganic acids or organic acids when there is a basic nitrogen atom. Examples of the salts of inorganic acids are hydrochlorides, sulfates, carbonates and nitrates and examples of the salts of organic acid are formates, acetates, propionates, oxalates, succinates, benzoates and paratoluenesulfonates. Further, the compound I may be a complex salt with metals such as calcium, zinc, magnesium, cobalt, copper or iron.

The compound I is produced, for example, by the following precesses.

The compound I is produced by allowing a carboxylic acid (II) of the formula:

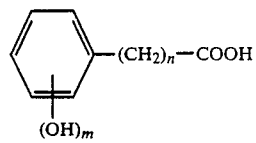

(wherein the symbols are the same as defined above), or salts or reactive derivatives thereof (referred to compound II hereinafter) to react with an amine compound (III) of the formula:

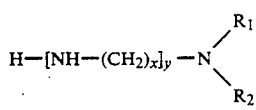

(wherein the symbols are the same as defined above), or salts thereof (referred to compund III hereinafter) and if necessary, eliminating protecting groups.

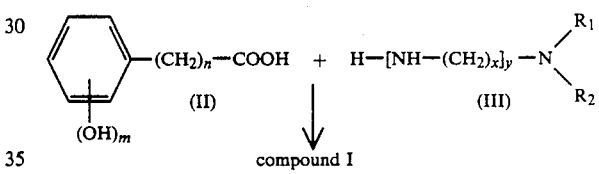

In the above formula, the starting compound (II) may be a salt or reactive derivative thereof. The starting compound (III) may be a salt. The salt of compound II include inorganic base salts or organic base salts of (II). Examples of the inorganic base salts of (II) are alkali metal salts, (e.g., sodium salt and potassium salt) and alkaline earth metal salts (e.g., calcium salt). Examples of the organic base salts of (II) are trimethylamine salt, triethylamine salt, tert.-butyldimethylamine salt, cyclohexylamine salt, dibenzylmethylamine salt, benzyldimethylamine salt, N,N-dimethylaniline salt, pyridine salt and quinoline salt. The reactive derivatives of the starting compound (II) mean reactive derivatives at the carboxyl group of the compound. The reactive derivatives of the compound II include acid halides, acid azides, acid anhydrides, mixed acid anhydrides, active amides, active esters and active thioesters. Examples of acid halides of (II) are acid chloride and acid bromide. Examples of the mixed acid anhydrides are monoalkylcarbonic acid-mixed acid anhydrides (e.g., mixed acid anhydrides of (II) with monomethylcarbonic acid, monoethylcarbonic acid, monoisopropylcarbonic acid, monoisobutylcarbonic acid, mono-tert.-butylcarbonic acid, monobenzylcarbonic acid, mono(p-nitrobenzyl)-carbonic acid or monoallylcarbonic acid), aliphatic carboxylic acid-mixed acid anhydrides (e.g., mixed acid anhydrides of (II) with acetic acid, trichloroacetic acid, cyanoacetic acid, propionic acid, butyric acid, isobutyric acid, valeric acid, isovaleric acid, pivalic acid, trifluoroacetic acid, trichloroacetic acid or acetoacetic acid), aromatic carboxylic acid-mixed acid anhydrides (e.g., mixed acid anhydrides of (II) with benzoic acid, p-toluic acid or p-chlorobenzoic acid) and organic sulfonic acid-mixed acid anhydrides (e.g., mixed acid anhydrides of (II) with methanesulfonic acid, ethanesulfonic acid, benzenesulfonic acid or p-toluenesulfonic acid). Examples of the active amides are amides with nitrogen-containing heterocyclic compounds (e.g., acid amides of (II) with pyrazole, imidazole or benzotriazole). These nitrogen-containing heterocyclic compounds may have a substituent such as an alkyl group, an alkoxy group, halogen atom, an oxo group, a thioxo group or an alkylthio group). The active esters of (II) may be any of those which are used for synthesis of peptides. Examples are, in addition to organic phosphates (e.g., diethoxy phosphate and diphenoxy phosphate), p-nitrophenyl ester, 2,4-dinitrophenyl ester, cyanomethyl ester, pentachlorophenyl ester, N-hydroxysuccinimide ester, N-hydroxyphthalimide ester, 1 hydroxybenzotriazole ester, 6-chloro-1-hydroxybenzotriazole ester and 1-hydroxy-1H-2-pyridone ester. Examples of the active thioesters of (II) include esters with aromatic heterocyclic thiol compounds (e.g., 2-pyridylthiol ester and 2-benzothiazolylthiol ester) and these heterocyclic rings may have substituents such as an alkyl group, an alkoxy group, halogen atom or an alkylthio group). One to three hydroxyl groups on the benzene ring of the starting compound (II) may be protected. As examples of the protecting groups, mention may be made of substituted or unsubstituted alkanoyl groups (e.g., acetyl, propionyl and trifluoroacetyl), substituted oxycarbonyl groups (e.g., methoxycarbonyl, ethoxycarbonyl, isopropoxycarbonyl, tert.-butoxycarbonyl, phenoxycarbonyl, benzyloxycarbonyl, p-methylbenzyloxycarbonyl or benzhydryloxycarbonyl), tert.-butyl group, aralkyl groups (e.g., benzyl, p-methylbenzyl, p-methoxybenzyl, p-chlorobenzyl, benzhydryl and trityl) and substituted silyl groups (e.g., trimethylsilyl and tert.-butyldimethylsilyl).

The salts of the compound III include salts of (III) with inorganic acids or organic acids. Examples of the inorganic acid salts include hydrochloride, hydrobromide, sulfate, nitrate and phosphate. Examples of the organic acid salts include formate, acetate, trifluoroacetate, methanesulfonate and p-toluenesulfonate. Preparation of salts or reactive derivatives of (II), that of salts of (III) and introduction of a protecting group into (II) are easily performed by known processes or processes similar thereto. For reaction between compound II and compound III, for example, reactive derivatives of starting compound (II) may be allowed to react with the compound III, after the former reactive derivatives are isolated from a reaction mixture. Alternatively, a reaction mixture as such which contains the reactive derivatives of starting compound (II) which are left unisolated may be allowed to react with the compound III. A reaction between the compounds III and II which are free acid or salts is effected in the presence of suitable condensation agents. The condensation agents include, for example, N,N'-disubstituted carbodiimides such as N,N'-dicyclohexylcarbodiimide, azolides such as N,N'-carbonyldiimidazole and N,N'-thiocarbonyldiimidazole, dehydrating agents such as N-ethoxycarbonyl-2-ethoxy-1,2-dihydroquinoline, phosphorus oxychloride, dimethylcyanophosphate, diethylcyanophosphate and alkoxyacetylene and 2-halogenopyridinium salts such as 2-chloropyridiniummethyl iodide and 2-fluoropyridiniummethyl iodide. In the case of using these condensation agents, the reaction is considered to proceed through the reactive derivative of (II). The reaction of the compound II and the compound III is usually carried out in a solvent. Suitable solvents are selected from those which do not harm the reaction. Examples of the solvent include ethers such as dioxane, tetrahyrofuran, diethyl ether, tert-butyl methyl ether, diisopropyl ether and ethylene glycol-dimethyl ether, esters such as ethyl formate, ethyl acetate and butyl acetate, halogenated hydrocarbons such as dichloromethane, chloroform, carbon tetrachloride, trichlene and 1,2-dichloroethane, hydrocarbons such as hexane, benzene and toluene, amides such as formamide, N,N-dimethylformamide and N,N-dimethylacetamide, ketones such as acetone, methyl ethyl ketone and methyl isobutyl ketone, nitriles such as acetonitrile and propionitrile. Besides, dimethylsulfoxide, sulfolane, hexamethylphosphoroamide or water may be used. The solvent may be alone or in mixture. The amount of the compound III used is usually 1–5 mol, preferably 1–3 mol per mol of starting compound (II). The reaction is effected at a temperature of $-80°$–$80°$ C., preferably $-40°$–$50°$ C., most preferably $-30°$–$30°$ C. The reaction time varies depending on the varieties of the compounds II and compounds III, variety of solvent (including mixing ratio in the case of mixed solvent) and reaction temperature, and is usually 1 minute–72 hours, preferably 15 minutes–3 hours. In the case where an acid halide of (II) is used as compound II, the reaction may be effected in the presence of deoxidizers for removal of hydrogen halide generated from the reaction system. As the deoxidizers, mention may be made of, for example, inorganic bases such as sodium carbonate, potassium carbonate, calcium carbonate and sodium bicarbonate, tertiary amines such as triethylamine, tripropylamine, tributylamine, diisopropylethylamine, cyclohexyldimethylamine, pyridine, lutidine, γ-collidine, N,N-dimethylaniline, N-methylpiperidine, N-methylpyrrolidine and N-methylmorpholine and alkylene oxides such as propylene oxide and epichlorohydrin. The starting compounds II and III are commercially available, or produced by known methods or similar methods.

The objective compound I of the present invention is obtained by allowing the compound II to react with the compound III as mentioned above and, if necessary, elimination of the protecting group and purification are effected. Elimination of the protecting group for hydroxyl groups is effected by a process as it is which is usually employed in the field of synthesis of peptides. For example, methoxycarbonyl, ethoxycarbonyl, tert.-butoxycarbonyl or phenoxycarbonyl is eliminated by acid (for example, hydrochloric acid or trifluoroacetic acid); benzyloxycarbonyl, p-methylbenzyloxycarbonyl or benzhydryloxycarbonyl is elimiated by catalytic reduction; benzyl, p-methylbenzyl, p-methoxybenzyl, p-chlorobenzyl, benzhydryl or trityl is eliminated by acids (for example, trifluoroacetic acid) or catalytic reduction and trimethylsilyl or tert.-butyldimethylsilyl is eliminated by water alone in the absence or the presence of acetic acid.

When elimination of the protecting group is carried out, elimination of the protecting group is effected after the hydroxyl group-protected compound I is isolated from a reaction mixture obtained from the reaction of the compound II and the compound III. Alternatively, the reaction mixture may be subjected as it is to elimination of the protecting group. Purification of the hydroxyl groupprotected compound I or the objective compound I of the present invention is carried out by the known purifying methods such as extraction, gel filtration, ion-exchange resin column chromatography, preparative thin-layer chromatography on silica gel, high-performance liquid chromatography and recrystallization.

Compound I has glutamate receptor-inhibiting activity. Therefore, compound I is important for research on isolation, structure elucidation and local analysis of the glutamate receptor. Further, the compound is expected to be useful for elucidation of mechanism of memory and cranial nerve diseases with which glutamic acid is associated. Accordingly, the compound I or a pharmaceutically acceptable salt thereof is useful as a medicine for therapy and/or for the prevention of the sequelae of cerebral apoplexy in warm-blooded animals, particuarly mammals (e.g. human, mouse, rat, cat, dog, rabitt, etc.).

The pharmaceutically acceptable salts include salts with inorganic acids or organic acids. Examples of the salts of inorganic acids are hydrochlorides, sulfates, carbonate and nitrates, and examples of the salts of organic acids are acetates, oxalates and succinates.

The compound I or salt thereof, when used as a medicine, may be administered orally or parenterally as it is, or in the form of a powder, granule, tablet, capsule, solution, suspension, emulsion, suppository or injection, which is prepared according to the conventional methods using pharmaceutically acceptable excipients, vehicles and diluents. The dose varies according to the animal, the sympton, the compound and the administration route; for example, the dose may be about 0.001 mg to 50 mg, preferably 1 mg to 5 mg of the compound of this invention per kg of body weight of a warm-blooded animal described above, in the case of oral administration, and may be administered one to three times per day.

The preparations are produced by per se known processes. The above-mentioned oral preparations, for example tablets, are produced by suitable combination with a binder (e.g. hydroxypropylcellulose, hydroxypropylmethylcellulose, macrogol, etc.), a disintegrator (e.g. starch, calcium carboxylmethylcellulose, etc.), or a lubricant (e.g. magnesium stearate, talc, etc.).

The parenteral preparations, for example injections, are produced by suitable combination with an isotonicity factor (e.g. glucose, D-sorbitol, D-mannitol, sodium chloride, etc.), an antiseptic (e.g. benzyl alcohol, chlorobutanol, methyl p-hydroxybenzoate, propyl p-hydroxybenzoate, etc.), or a buffer (e.g. phosphate buffer, sodium acetate buffer, etc.).

The invention is further illustrated by the following specific examples.

EXAMPLE 1

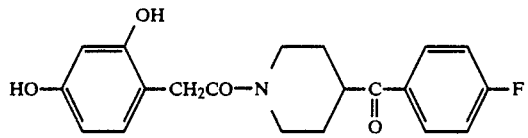

1-(2,4-Dihydroxyphenylacetyl)-4-(4-fluorobenzoyl) piperidine (i) To solution (20 ml) of 4-(4-fluorobenzoyl) piperidine. hydrochloride (670 mg) and 2,4-dibenzoyloxyphenylacetic acid (1.0 g) in N,N-dimethylformamide are added triethylamine (1.2 ml) and diethyl cyanophosphate (561 mg) and the mixture is stirred at room temperature for 10 minutes. To the reaction solution is added water and the mixture stirred for 20 minutes. The product is extracted with dichloromethane. The dichloromethane layer is washed with water and dried over anhydrous sodium sulfate, and then the solvent is distilled off. The residue is purified by silica gel column chromatography. The crude product is obtained from a fraction eluted with dichloromethane-ethyl acetate mixture (2:1). Recrystallization of the product from dichloromethane-diethyl ether mixture yields 1-(2,4-dibenzyloxyphenylacetyl)-4-(4-fluorobenzoyl)piperidine (1.25 g) in the colorless columnar crystal form.

Melting point 158°–159° C.

Elemental analysis for $C_{34}H_{32}FNO_4$: Calcd. C: 75.96; H: 6.00; N: 2.61 Found C: 75.76; H: 5.96; N: 2.78

IR spectrum $\nu_{max}$ (KBr)cm$^{-1}$: 1680 (C=O), 1640 (C=O), 1600 (Ar).

NMR spectrum $\delta_{ppm}$ (CDCl$_3$): 1.3–2.0 (4H, m), 2.5–3.5 (5H, m), 3.7–4.7 (2H, m), 5.00 (4H, s), 6.4–8.1 (17H, m).

(ii) To a solution (30 ml) of 1-(2,4-dibenzyloxyphenylacetyl)-4-(4-fluorobenzoyl)piperidine (250 mg) obtained in (i) above in ethanol is added 10% palladium-carbon (30 mg). Catalytic reduction is effected in a hydrogen stream at room temperature under atmospheric pressure for 3 hours. The catalyst is removed by filtration and then the filtrate is concentrated under reduced pressure. The oily matter obtained is digested with ether to obtain colorless powder. The product is filtered and subjected to dryness to yield 1-(2,4-dihydroxyphenylacetyl)-4-(4-fluorobenzoyl)piperidine (150 mg)

Mass spectrum : m/z=357 (M$^+$)

Elemental analysis for $C_{20}H_{20}FNO_4$: Calcd. C: 67.21; H: 5.64; N: 3.92 Found C: 69.93; H: 5.63; N: 3.70

IR spectrum $\nu_{max}$ (KBr)cm$^{-1}$: 3300 (OH), 1670 (C=O), 1630 (C=O), 1605 (Ar).

EXAMPLE 2

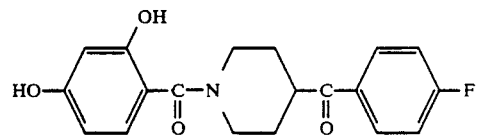

1-(2,4-Dihydroxybenzoyl)-4-(4-fluorobenzoyl) piperidine (i) To solution (20 ml) of 4-(4-fluorobenzoyl) piperidine.hydrochloride (670 mg) and 2,4-dibenzyloxybenzoic acid (960 mg) in N,N-dimethylformamide are added triethylamine (1.2 ml) and diethylcyanophosphate (570 mg). The mixture is stirred at room temperature for 15 minutes. The same procedures as in Example 1, (i) is carried out to obtain 1-(2,4-dibenzyloxybenzoyl)-4-(4-fluorobenzoyl)pipieridine (1.15 g) in the colorless columnar crystal form.

Melting point: 139°–140° C.

Elemental analysis for $C_{33}H_{30}FNO_4$: Calcd. C: 75.70; H: 5.78; N: 2.68. Found C: 75.87; H: 5.69; N: 2.73

IR spectrum $\nu_{max}$(KBr)cm$^{-1}$: 1680 (C=O), 1620 (C=O), 1600 (Ar).

NMR spectrum δ ppm (CDCL$_3$): 2.0–1.5 (4H, m), 2.83–3.50 (5H, m), 3.5–4.9 (2H, m), 5.03(2H, s), 5.05 (2H, s), 6.5–8.1 (17H, m).

(ii) 1-(2,4-Dibenzyloxybenzoyl)-4-(4-fluorobenzoyl) piperidine (307 mg) obtained in (i) above is subjected to catalytic reduction in the same manner as in Example 1, (ii) to yield 1-(2,4-dihydroxybeozoyl)-4-(4-fluorobenzoyl) piperidine (177 mg) in the powder form.

Mass: m/z=343 (M+)

Elemental analysis for $C_{19}H_{18}FNO_4$; Calcd. C: 66.46; H: 5.28; N: 4.08. Found C: 66.67; H: 5.33; N: 3.89.

IR spectrum $\nu_{max}$(KBr) cm$^{-1}$: 3350 (OH), 1640 (C=O), 1630 (C=O), 1600 (Ar).

EXAMPLE 3

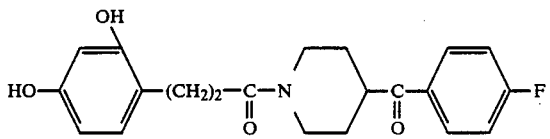

1-[3-(2,4-Dihydroxyphenyl)propionyl]-4-(4-fluorobenzoyl)piperidine (i) Condensation between 4-(4-fluorobenzoyl) piperidine.hydrochloride (682 mg) and 3-(2,4-dibenzyloxyphenyl)propionic acid (1.04 g) is carried out in the same manner as in Example 1, (i) to yield 1-[3-(2,4-dibenzyloxyphenyl)propionyl]-4-(4-fluorobenzoyl)-piperidine (1.20 g) in the colorless columnar crystal form.

Melting point: 140°–141° C.

Elemental analysis for $C_{35}H_{34}FNO_4$: Calcd. C: 76.20; H: 6.21; N: 2.54. Found C: 76.16; H: 6.20 N: 2.76.

IR spectrum $\nu_{max}$ (KBr) cm$^{-1}$: 1680 (C=O), 1630 (C=O), 1600 (Ar).

NMR spectrum δ ppm (CDCl$_3$): 1.0–1.9 (4H, m), 2.7–4.8 (5H, m), 2.3–3.00 (4H, m), 4.96 (4H, s), 6.3–8.1 (17H, m).

(ii) 1-[3-(2,4-Dibenzyloxyphenyl)propionyl]-4-(4-fluorobenzoyl)piperidine (400 mg) is subjected to catalytic reduction in the same manner as in Example 1, (ii) to yield 1-[3-(2,4-dihydroxyphenyl)propionyl]-4-(4-fluorobenzoyl)piperidine (232 mg).

Mass: m/z=371 (M+)

Elemental analysis for $C_{21}H_{22}FNO_4$: Calcd. C: 67.91; H: 5.97; N: 3.77. Found C: 68.10 H: 5.89; N: 3.63.

IR spectrum $\nu_{max}$ (KBr) cm$^{-1}$: 3300 (OH), 1660 (C=O), 1630 (C=O), 1605 (Ar).

EXAMPLE 4

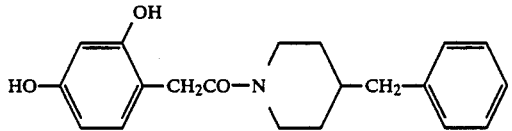

1-(2,4-Dihydroxyphenylacetyl)-4-benzylpiperidine (i) To a solution (20 ml) of 4-benzylpiperidine (423 mg) and 2,4-dibenzyloxyphenylacetic acid (700 mg) in N,N-dimethylformamide are added triethylamine (0.56 ml) and diethyl cyanophosphate (393 mg) and the mixture is stirred at room temperature for 15 minutes. Water is added and stirring carried out for 10 minutes, followed by extraction of the product with dichloromethane. The dichloromethane layer is washed with water and dried over anhydrous sodium sulfate. The solvent is distilled off. The residue is subjected to purification by silica gel column chromatography. 1-(2,4-Dibenzyloxyphenylacetyl)-4-benzylpiperidine (1.0 g) in the colorless oily form is obtained from a fraction eluted with dichloromethane-ethyl acetate mixture (8:1).

Elemental analysis for $C_{34}H_{35}NO_3$: Calcd. C: 80.76; H: 6.98; N: 2.77. Found C: 81.82; H: 7.10; N: 2.68.

IR spectrum $\nu_{max}$ (Neat) cm$^{-1}$: 1640 (C=O), 1600 (Ar).

NMR spectrum δ ppm (CDCl$_3$): 0.9–1.9 (4H, m), 2.1 – 3.0 (5H, m), 3.62 (2H, s), 5.0–5.1 (4H, br. s), 6.5–8.1 (18H, m).

(ii) To a solution (30 ml) of 1-(2,4-dibenzyloxyphenylacetyl)-4-benzylpiperidine (360 mg) obtained in i) above in ethanol is added 10% palladium-carbon (45 mg). The mixture is subjected to catalytic reduction in hydrogen gas at room temperature under atmospheric pressure. The catalyst is filtered and the filtrate is concentrated under reduced pressure to yield a colorless candy-like product. This product is dried under reduced pressure with a vacuum pump to obtain 1-(2,4-dihydroxyphenylacetyl)-4-benzylpiperidine (265 mg) in the powder form.

Mass: m/z=325 (M+)

Elemental analysis for $C_{20}H_{23}NO_3 \cdot H_2O$ : Calcd C: 69.95; H: 7.33; N: 4.08. Found C: 69.83; H: 7.48; N: 3.93.

IR spectrum $\nu_{max}$ (KBr)-$^1$: 3300 (H$_2$), 1650 (C=O), 1600 (Ar).

EXAMPLE 5

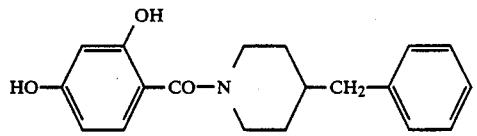

1-(2,4-Dihydroxybenzoyl)-4-benzylpiperidine i) Condensation between 4-benzylpiperidine (438 mg) and 2,4-dibenzyloxybenzoic acid is carried out in the same manner as in Example 4, i) to obtain 1-(2,4-dibenzyloxybenzoyl)-4-benzylpiperidine (1.0 g) in the colorless oily form.

Elemental analysis $C_{33}H_{33}NO_3$: Calcd. C: 80.62; H: 6.77; N: 2.85. Found C: 80.57; H: 6.80; N: 2.93.

IR spectrum $\nu_{max}$ (Neat) cm$^{-1}$: 1740 (C=O), 1620 (Ar). 20 NMR spectrum δ ppm (CDCl$_3$): 0.8–1.8 (4H, m), 1.9–3.0 (5H, m). 5.03 (4H, s), 6.4–7.8 (18H, m).

ii) 1-(2,4-Dibenzyloxybenzoyl)-4-benzylpiperidine (360 mg) is subjected to catalytic reduction in the same manner as in Example 4, ii) to obtain 1-(2,4-dihydroxybenzoyl)-4-benzylpiperidine (216 mg) in the colorless powder form.

Mass : m/z=311 (M+)

Elemental analysis for $C_{19}H_{21}NO_3$: Calcd. C: 73.29; H: 6.80; N: 4.50. Found C: 73.36; H: 6.81; N: 4.42.

IR spectrum $\nu_{max}$ (KBr) cm$^{-1}$: 1650 (C=O), 1610 (Ar).

EXAMPLE 6

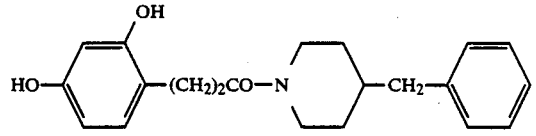

1-[3-2,4-Dihydroxyphenyl)propionyl]-4-benzyl-piperidine i) Condensation between 4-benzylpiperidine (438 mg) and 3-(2,4-dibenzylphenyl)propionic acid (754 mg) is carried our in the same manner as in Example 4, i) to yield 1-[3-(2,4-dibenzyloxyphenyl)propionyl]-4-benzylpiperidine (900 mg) in the colorless needle-like crystal form.

Melting point: 102°–103° C.

Elemental analysis for $C_{35}H_{37}NO_3$: Calcd. C: 80.89; H: 7.18; N: 2.70 . Found C: 80.83; H: 7.20; N: 2.89.

IR spectrum $\nu_{max\,(KBr)}\,cm^{-1}$: 1640 (C=O), 1600 (Ar).

NMR spectrum $\nu$ ppm (CDCl$_3$): 0.9–1.9 (4H, m), 2.3–2.6 (5H, m), 5.03 (4H, s), 6.4–7.6 (18H, m).

(ii) 1-[3-(2,4-Dibenzyloxyphenyl)propionyl]-4-benzylpiperidine (415 mg) is subjected to catalytic reduction in the same manner as in Example 4, ii) to obtain 1-[3-(2,4-dihydroxyphenyl)propionyl]-4-benzylpiperidine (274 mg) in the powder form.

Mass: m/z=339 (M$^+$)

Elemental analysis for $C_{21}H_{25}NO_3 \cdot H_2O$ Calcd. C: 70.56; H: 7.61; N: 3.92 . Found C: 70.71; H: 7.60; N: 3.78.

IR spectrum $\nu_{max}$ (KBr) cm$^{-1}$: 1670 (C=O), 1605 (Ar).

EXAMPLE 7

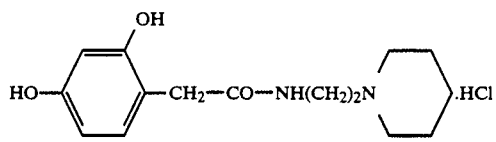

1-[2-(2,4-Dihydroxyphenylacetyl)aminoethyl]piperidine hydrochloride (i) To a solution of 1-(2-aminoethyl)piperidine (368 mg) and 2,4-dibenzyloxyphenylacetic acid (1.0 g) in N,N-dimethylformamide are added triethylamine (1.2 ml) and diethylcyanophosphate (561 mg) in sequence. The mixture is stirred at room temperature for 30 minutes. To the reaction solution is added water and stirring carried out for 10 minutes. The product is extracted with dichloromethane. The dichloromethane layer is washed with water and dried over anhydrous sodium sulfate. The solvent is distilled off and the residue obtained is purified by silica gel column chromatography. The fractions eluted with dichloro-methane-methanol mixture (10 : 1) is recrystallized from dichloromethane-n-hexane mixture (1 : 5) to obtain 1-[2-(2,4-dibenzyloxyphenylacetyl)aminoethyl]piperidine (950 mg) in the colorless needle-like crystal form.

Melting point: 149°–151° C. Elemental analysis for $C_{29}H_{34}N_2O_3$: Calcd. C: 75.95; H: 7.47; N: 6.11. Found C: 75.70; H: 7.34; N: 6.21.

IR spectrum $\nu_{max}$ (KBr) cm$^{-1}$: 3300 (NH), 1640 (C=O), 1600 (Ar).

NMR spectrum δ ppm (CDCl$_3$): 1.36 (6H, s), 2.1 2.4 (6H, m), 3.22 (2H, s), 3.53( 2H, s), 5.03 (2H, s), 5.06 (2H, s), 6.5–7.5 (13H, m).

(ii) To solution of 1-[2-(2,4-dibenzyloxyphenylacetyl)aminoethyl]piperidine (430 mg) obtained in i) above in 1% hydrochloric acid-ethanol mixture (20 ml) is added 1% palladium-carbon (60 mg). Catalytic reduction is effected in a hydrogen stream at room temperature under atmospheric pressure. The catalyst is removed by filtration and the filtrate is concentrated to obtain a colorless, glass like product. This product is digested with ether to obtain powder. The product is filtered and dried to yield 1-[2-(2,4-dihydroxyphenylacetyl)aminoethyl]piperidine.hydrochloride (278 mg).

SIMS Mass: m/z=279 (M$^+$+H$^+$)

Elemental analysis for $C_{15}H_{22}N_2O_3 \cdot HCl \cdot H_2$: Calcd. C: 54.13; H: 7.57; N: 8.42. Found C: 53.89; H: 7.68; N: 8.29.

IR spectrum $\nu_{max}$ (KBr) cm$^{-1}$: 2800, 1630 (C=O), 1605 (Ar).

EXAMPLE 8

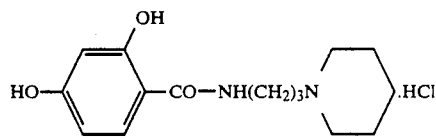

1-[3-(2,4-Dihydroxybenzoly)aminopropyl]piperidine. hydrochloride (i) Condensation between 1-(3-aminopropyl) piperidine (427 mg) and 2,4-dibenzoyloxybenzoic acid (1.0 g) is carried out in the same manner as in Example 7, i) to yield 1-[3-(2,4-dibenzyloxybenzoyl)aminopropyl]piperidine (1.2 g).

Melting point: 103–104 ° C.

Elemental analysis for $C_{29}H_{34}N_2O_3$: Cacld. C: 75.95; H: 7.47; N: 6.11. Found C: 75.96; H: 7.50; N: 6.08.

(ii) 1-[3-(2,4-Dibenzyloxybenzoyl)aminopropyl]-piperidine (650 mg) obtained in i) above was subjected to catalytic reduction in the same manner as in Example 7, ii) to yield 1-[3-(2,4-dihydroxybenzoyl)aminopropyl]-piperidine. hydrochloride (426 mg) in a powder.

SIMS Mass: m/z=279 (M$^+$+H$^+$)

Elemental analysis for $C_{15}H_{22}N_2O_3 \cdot HCl \cdot \frac{1}{2}H_2O$: Calcd. C: 55.63; H: 7.47; N: 8.65. Found C: 55.89; H: 7.61; N: 8.47.

IR spectrum $\nu_{max}$ (KBr) cm$^{-1}$: 2850, 1640 (C=O), 1605 (Ar).

EXAMPLE 9

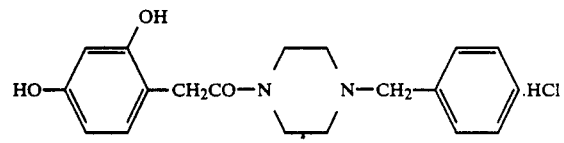

1-(2,4-Dihydroxyphenylacetyl)-4-benzylpiperazine hydrochloride (i) To solution (15 ml) of 2,4-dibenzyloxyphenyl acetic acid (760 mg) and 1-benzylpiperazine (440 mg) in N,N-dimethylformamide are added triethylamine (0.6 ml) and diethyl cyanophosphate (420 mg) at 5° C. under stirring and stirring is continued for 15 minutes. To the reaction solution is added water and the product is extracted with dichloromethane. The dichloromethane layer is washed with water and dried. The solvent is distilled off to yield 1-(2,4-dibenzyloxyphenylacetyl)-4-benzylpiperazine (968 mg).

Melting point: 104–106 ° C.

Elemental analysis for $C_{33}H_{34}N_2O_3$: Calcd. C: 78.23; H: 6.76; N: 5.53. Found C: 78.40; H: 6.88; N: 5.49.

IR spectrum $\nu_{max}$ (KBr) cm$^{-1}$: 1640 (C=O), 1605 (Ar).

(ii) To 1-(2,4-dibenzyloxyphenylacetyl)-4-benzylpiperazine (620 mg) obtained in i) above in 1% hydrochloric acid-ethanol mixture (20 ml) is added 10% palladium-carbon (75 mg) and the mixture is subjected to catalytic reduction in a hydrogen stream at room temperature under atmospheric pressure. The reaction terminates at a point where two molar equivalents of hydrogen are absorbed. The catalyst is removed by filtration and the filtrate is concentrated under reduced pressure. To the residue is added ether to digest and powder is obtained. This is filtered and dried to obtain 1-(2,4-dihydroxyphenylacetyl)-4-benzylpiperazine.hydrochloride (384 mg).

Mass: m/z=362 (M+)

Elemental analysis for $C_{19}H_{22}N_2O_3$ HCl: Calcd. C: 62.89; H: 6.39; N: 7.72. Found C: 62.87; H: 6.69; N: 7.56.

EXAMPLE 10

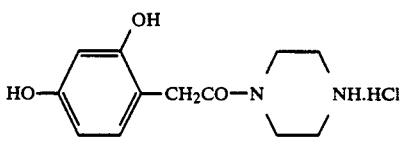

1-(2,4-Dihydroxyphenylacetyl)piperazine.hydrochoride

To a solution (10 ml) of 1-(2,4-dihydroxyphenylacetyl)-4-benzylpiperazine.hydrochloride (160 mg) obtained in Example 9, ii) in ethanol is added palladium-black (30 mg) to subject to catalytic reduction in hydrogen at 40° C. under twice atmospheric pressure for 10 hours. The catalyst is removed by filtration and the filtrate is concentrated under reduced pressure. The glass-like substance obtained is digested with ether into powder. This is filtered and dried to obtain 1-(2,4-dihydroxyphenylacetyl)piperazine.hydrochloride (147 mg).

SIMS Mass: m/z=267 (M+ +H+)

Elemental analysis for $C_{12}H_{16}N_2O_3$.HCl.H$_2$O: Calcd. C: 49.57; H: 6.59; N: 9.64. Found C: 49.80; H: 6.66; N: 9.55.

EXAMPLE 11

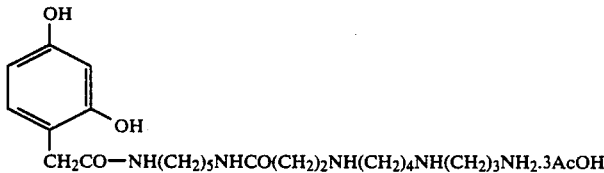

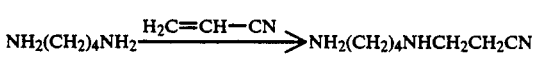

18-(N-2,4-dihydroxyphenylacetyl)amino-4,9,13-triaza-12-oxo-1-aminooctadecane triacetate $$NH_2(CH_2)_4NH_2 \xrightarrow{H_2C=CH-CN} NH_2(CH_2)_4NHCH_2CH_2CN \quad (i)$$

To 1,4-diaminobutane (84.6 g) cooled on ice is added dropwise acrylonitrile(50.9 g). After dropping is over, the reaction solution is stirred for 20 minutes under ice cooling, followed by stirring at 40° C. for one hour and then at 100° C. for three hours. The product is distilled under reduced pressure and purified to yield 1-(N-2-cyano-ethyl)amino-4-aminobutane (66 g) in the colorless oily form.

B.p: 120–121° C./1.7 mmHg.

Elemental analysis for $C_7H_{15}N_3$: Calcd. C: 59.53; H: 10.71; N: 29.76. Found C: 59.61; H: 10.66; N: 29.62.

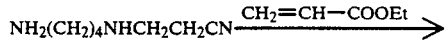

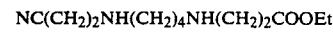

To 1-(N-2-cyanoethyl)amino-4-aminobutane (62.8 g) in ethanol is gradually added a solution (200 ml) of ethyl acrylate(48.2 g) in ethanol. The reaction solution is heated under refluxing for two hours and the solvent is distilled off under reduced pressure to yield 1-(N-2-cyanoethyl)amino-4-(N-2-ethoxycarbonylethyl)aminobutane (108 g).

IR $\nu_{neat}$ (cm$^{-1}$): 1730 (C=O), 2260 (CN) Elemental analysis for $C_{12}H_{23}N_3O_2$: Calcd. C: 59.72; H: 9.61; N: 17.41. Found C: 59.64; H: 9.70; N: 17.36.

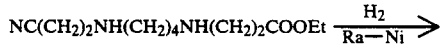

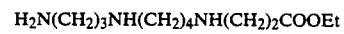

To a solution (600 ml) of 1-(N-2-cyanoethyl)amino-4-(N-ethoxycarbonylethyl)aminobutane (60 g) in ethanol is added Raney-nickel (30 g) and reduction is conducted in an autoclave at reaction temperature (25° C.) under hydrogen pressure (100 kg/cm$^2$) for three hours. After the reaction is over, the catalyst is removed by filtration and the filtrate is concentrated under reduced pressure to obtain 1-(N-3-aminopropyl)amino-4-(N-2-ethoxycarbonylethyl)aminobutane (60 g) in the colorless oily form. IR $\nu_{neat}$ (cm$^{-1}$): 1725 (C=O)

NMR δ ppm (CDCl$_3$): 1.26 (t, 3H), 1.2–1.8 (m. 6H), 2.3–3.0 (m, 12H), 4.14 (q, 2H).

Elemental analysis for $C_{12}H_{27}N_3O_2$: Calcd. C: 58.74; H: 11.09; N: 17.13. Found C: 58.80; H: 10.83; N: 16.88.

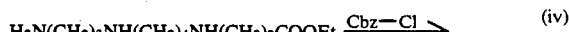

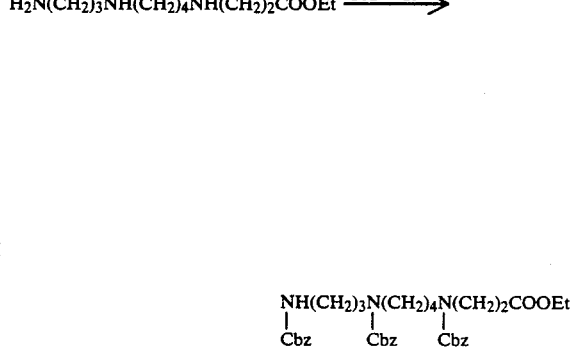

wherein

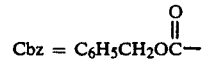

To solution (200 ml) of 1-(N-3-aminopropyl)amino-4-(N-2-ethoxycarbonylethyl)aminobutane (12.2 g) in dichloromethane is added triethylamine (28 ml). Then, benzyloxycarbonyl chloride (Cbz-Cl) (29 ml) is gradually added dropwise thereto with stirring under ice cooling. The reaction solution is stirred at room temperature for 12 hours, followed by washing with saturated aqueous sodium hydrogencarbonate solution and 1N aqueous hydrochloric acid solution in this order. Drying is carried out over anhydrous magnesium sulfate. The solvent is distilled off to obtain a colorless oily product. This is purified by silica gel column chromatography. The fraction eluted with dichloro-methane-methanol (20:1) yields 1-(N-2-ethoxycarbonylethyl, N-benzyloxycarbonyl)amino-4-[N-3-(N-benzyloxycarbonyl)aminopropyl, N-benzyloxycarbonyl]aminobutane (16.0 g) in the colorless oily form.

NMR δ ppm (CDCl₃): 1.20 (t, 3H), 1.1–1.8 (m, 6H), 2.53 (t, 2H), 2.9–3.6 (m, 10H), 4.27 (q, 2H), 5.10 (s, 6H), 7.33 (m, 15H).

Elemental analysis for $C_{36}H_{45}N_3O_8$: Calcd. C: 66.75; H: 7.00; N: 6.49. Found C: 66.79; H: 7.12; N: 6.32.

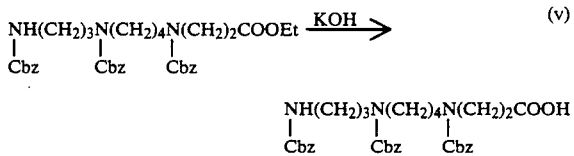

A solution (68 ml) of 1-(N-2-ethoxycarbonylethyl, N-benzyloxycarbonyl)amino-4- N-3-(N-benzyloxycarbonyl)aminopropyl, N-benzyloxycarbonyl aminobutane (21 g) in 1N potassium hydroxide-ethanol mixture is stirred at room temperature for two hours. To the reaction solution is added water (100 ml) and the mixture is washed twice with 100 ml of ether. The aqueous phase is made acidic with 1N aqueous hydrochloric acid solution and the product is extracted with ethyl acetate. The ethyl acetate layer is washed with water and dried over anhydrous magnesium sulfate. The ethyl acetate layer is distilled off under reduced pressure to yield $N^4,N^9, N^{13}$-tribenzyl-oxycarbonyl-4,9,13-triazatridecanoic acid in colorless powder (16.3 g).

Elemental analysis for $C_{34}H_{41}N_3O_8$: Calcd. C: 65.89; H: 6.67; N: 6.78. Found C: 65.77; H: 6.39; N: 6.60.

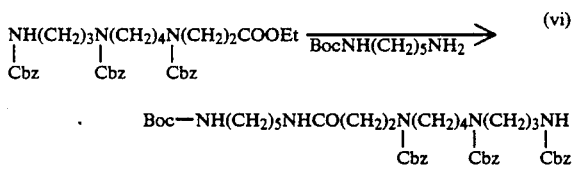

wherein

To a solution (100 ml) of N-(tert.-butoxycarbonyl)-cadaverine (2.2 g) and $N^4,N^9,N^{13}$-tribenzyloxycarbonyl-4,9,13-triazatridecanoic acid (6.7 g) in acetonitrile are added N-hydroxybenztriazole (1.46 g) and dicyclohexylcarbodiimide (2.43 g) with stirring under ice cooling. The reaction solution is stirred at room temperature for 12 hours and precipitate is removed by filtration. The filtrate is concentrated under reduced pressure to give an oily matter. This is dissolved in dichloromethane (200 ml) and washed with 10 % aqueous citric acid solution, saturated aqueous sodium hydrogencarbonate solution and water, in this order. The dichloromethane layer is dried over anhydrous magnesium sulfate and the solvent is distilled off under reduced pressure to yield an oily product. The product is purified by silica gel column chromatography. 1-(N-benzyloxycarbonyl)amino- 18-(N-tert.-butoxycarbonyl)-amino-$N^4$, $N^9$-dibenzyloxycarbonyl-4,9,13-triaza-12-oxooctadecane (2.8 g) in the colorless oily form is obtained from a fraction eluted with dichloromethane-methanol (30:1).

NMR δ ppm (CDCl₃) : 1.1–1.9(m,12H), 1.43(s,9H), 2.37(t,2H), 2.9–3.7(m,14H), 5.10(s,6H), 7.35(m,15H).

Elemental analysis for $C_{44}H_{61}N_5O_9$: Calcd. C: 65.73; H: 7.65; N: 8.71. Found C: 65.54; H: 7.70; N: 8.50.

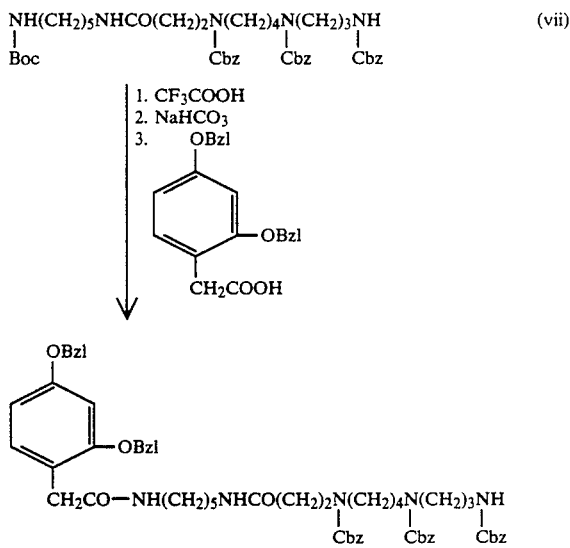

wherein

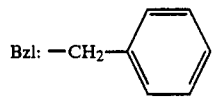

1-(N-benzyloxycarbonyl)amino-18-(N-tert.butoxycarbonyl $N^4,N_9$-dibenzyloxycarbonyl-4,9,13-triaza-12-oxooctadecane (1.24 g) is dissolved in trifluoroacetic acid (10 ml). The solution is stirred at room temperature for 10 minutes and then dichloromethane (100 ml) is added thereto. To this is added saturated aqueous sodium hydrogencarbonate solution to adjust to pH 9.0. The organic phase is separated and dried over anhydrous magnesium sulfate. The solvent is distilled off to yield an oily product (1.13 g). To the product are added 2,4-dihydroxyphenylacetic acid (590 mg), N-hydroxybenztriazole (332 mg) and dicyclohexylcarbodiimide (382 mg), in this order. The reaction solution is stirred at room temperature for five hours. After the reaction is over, precipitate produced is removed by filtration and the filtrate is concentrated. The oily matter obtained is dissolved in ethyl acetate (100 ml) and washed with aqueous 0.5 N hydrochloric acid solution, saturated aqueous sodium hydrogencarbonate solution and water, in this order. The ethyl acetate layer is dried over anhydrous magnesium sulfate and then the solvent is distilled off. The residue is allowed to precipitate again with ethyl acetate-ether mixture (1:2) for purification, to obtain 18-(N-2,3-dibenzyloxyphenylacetyl)amino-1-(N-benzyloxycarbonyl)amino-$N^4,N^9$-dibenzyloxycarbonyl-4,9,13-triaza-12-oxooctadecane (800 mg) in colorless powder.

Melting point 75–78 °C.
Elemental analysis for $C_{61}H_{71}N_5O_{10}$: Calcd. C: 70.84; H: 6.92; N: 6.77. Found C: 70.63; H: 6.69; N: 6.60.
IR $\nu_{KBr}$: 1700, 1640 (C=O)

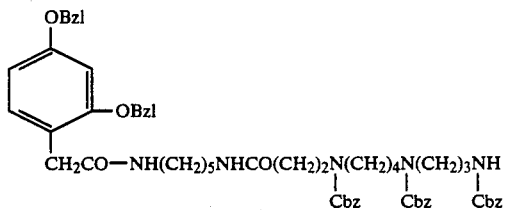

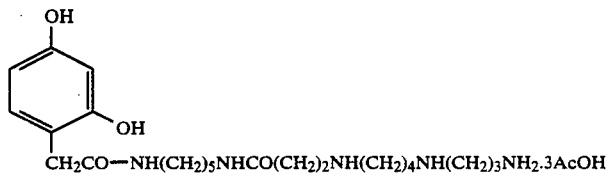

To a solution (50 ml) of protector, 1-(N-benzyloxycarbonyl)amino-18-(N-2,4-dibenzyloxyphenylacetyl)-amino-$N^{4,}N^9$-dibenzyloxycarbonyl-4,9,13-triaza-12-oxooctadecane (310 mg) in methanol are added acetic acid (0.06 ml) and 10 % palladium-carbon (100 mg). Catalytic reduction is conducted in a hydrogen stream at room temperature for 36 hours. The catalyst is removed by filtration and the filtrate is concentrated under reduced pressure to yield a glass-like product. The product is purified by column chromatography using Sephadex LH-20. The fraction eluted with 0.1 N acetic acid in distilled water is collected and lyophilized to yield 18-(N-3,4-dihydroxypehnylacetyl)amino-4,9,13-triaza-12-oxo-1-aminooctadecane triacetate (144 mg) in the colorless glass-like form.
SIMS : m/z=452[M++H+]($C_{23}H_4N_{54}$: M=451).

EXAMPLE 12

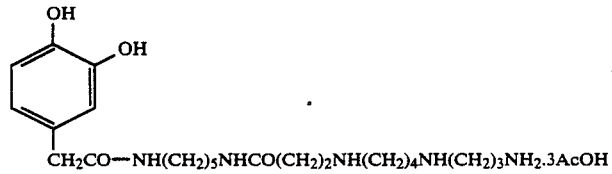

18-N-3,4-Dihydroxyphenylacetyl)amino-4,9,13-triaza-12-oxo-1-aminooctadecane.triacetate

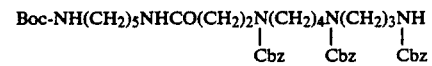

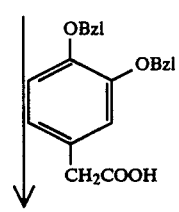

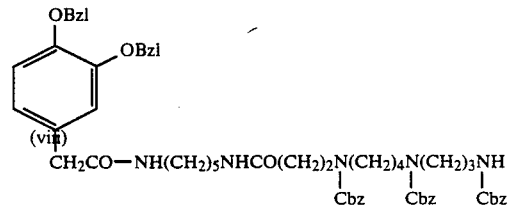

-continued (a) To a solution (30 ml) of 3,4-dibenzyloxyphenylacetic acid (651 mg) in acetronitrile solution are added N-hydroxybenztriazole (345 mg) and dicyclohexylcarbodiimide (386 mg) and the mixture is stirred at room temperature for two hours. The precipitate produced is removed by filtration and the filtrate is concentrated under reduced pressure. To the residue is added acetonitrile (15 ml) and the insoluble matter is again removed by filtration. The filtrate is used in the following reaction b).

(b) A solution of 1-(N-benzyloxycarbonyl)amino-18-(N-tert.-butyloxycarbonyl)amino-$N^{4,}N^9$-dibenzyloxycarbonyl-4,9,13-triaza-12-oxooctadecane (1.42 g) in trifluoroacetic acid (3ml) is stirred at room temperature for 30 minutes. To the reaction solution is added toluene (50 ml) and the solvent is distilled off under reduced pressure. To the residue is added ether and then stirring results in a white precipitate. This is obtained by filtration and dried. The product is dissolved in acetonitrile (20 ml), and thereto is added triethylamine (0.31 ml) under ice cooling with stirring. N,N-dimethylformaldehyde (1 ml) is further added thereto and then the acetonitrile solution obtained in (a) above is added. The reaction solution is stirred at room temperature for three hours. The resulting crystalline powder is filtered and dried to yield 1-(N-benzyloxycarbonyl)amino-18-(N-3,4-dibenzyloxyphenylacetyl $N^4,N^9$-dibenzyloxycarbonyl-4,9,13-triaza-12-oxooctadecane (775 mg) in colorless crystallized powder.

Melting point 93–96 ° C.

Elemental analysis for $C_{61}H_{71}N_5O_{10}$: Calcd. C: 70.84; H: 6.92; N: 6.77. Found C: 70.80; H: 7.18; N: 6.54.

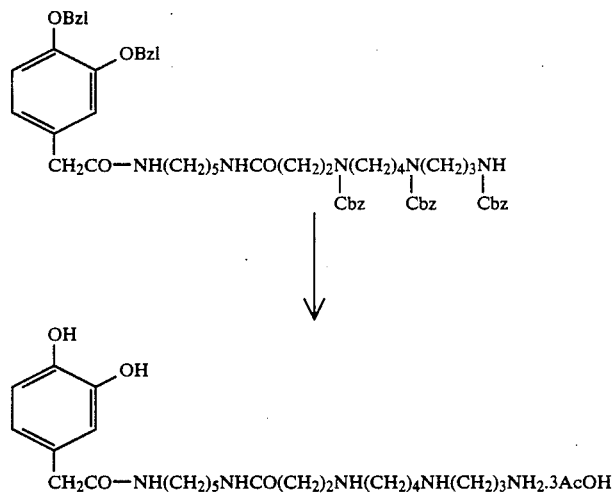

To a solution (25 ml) of protector, 1-(N-benzyloxycarbonyl)amino-18-(N-3,4-dibenzyloxyphenylacetyl)amino-$N^4,N^9$-dibenzyloxycarbonyl-4,9,13-triaza-12-oxooctadecane (263 mg) in ethanol are added acetic acid (0.05 ml) and 10 % palladium-carbon (68 mg). Catalytic reduction is effected in a hydrogen stream at room temperature for 24 hours. The catalyst is removed by filtration and the filtrate is concentrated under reduced pressure to yield a glass-like product. The product is purified by column chromatography using Sephadex LH-20. The fraction eluted with 0.1 N acetic acid in distilled water is collected and lyophilized to yield 18-(N-3,4-dihydroxyphenylacetyl)amino-4,9,13-triaza-12-oxo-1-aminooctadecane.triacetate (89 mg).

SIMS : m/z=452 [$M^+ + H^+$] ($C_{23}H_{41}N_5O_4$: M=451).

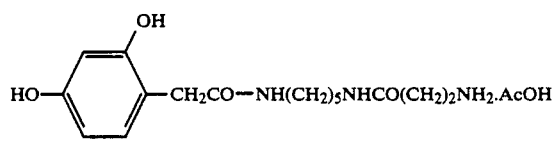

EXAMPLE 13

1-(2,4-Dihydroxyphenylacetyl)amino-5-(3-aminopropionyl) aminopentane.acetate

To a solution (50 ml) of 5-amino-1-pentanol (10 g) in dioxane is added tert.-butyl 4,6-dimethylpyrimidine-2-yl thiol carbonate (Boc.- SDP) (23.31 g) and the mixture is stirred at room temperature for 12 hours. The solvent is distilled off and the residue is dissolved in ethyl acetate (300 ml). The ethyl acetate layer is washed with aqueous 1N hydrochloric acid solution and dried over anhydrous sodium sulfate. The solvent is distilled off to obtain oily, colorless 5-(N-tert.-butoxycarbonyl)amino-1-pentanol (14.3 g).

Elemental analysis for $C_{10}H_{21}NO_3$: Calcd. C: 66.90; H: 8.42; N: 5.57. Found C: 66.77; H: 8.19; N: 5.36.

(ii)

To solution (300 ml) of 5-(N-tert.-butoxycarbonyl)amino-1-pentanol (21.3 g) in anhydrous tetrahydrofuran are added triphenylphosphin (54.9 g), phthalimide (30.8 g) and dimethylazodiformate (30.6 g) under ice cooling with stirring. The reaction solution is stirred at room temperature for three hours and the solvent is distilled off under reduced pressure. The residue is extracted with n-hexane-ethyl acetate mixture (2:1). The organic layer is concentrated under reduced pressure to yield a colorless oily product. This is purified by silica gel column chromatography. N-[5-(N-tert.-butoxycarbonyl)amino]pentylphthalimide (22.5 g) is obtained from a fraction eluted with n-hexane-ethyl acetate mixture (2:1).

Melting point 81°–83 ° C.

Elemental analysis for $C_{18}H_{24}N_2O_4$: Calcd C: 65.04; H: 7.28; N: 8.43. Found C: 64.87; H: 7.02; N: 8.70.

(iii)

To a solution (500 ml) of N-[5-(N-butoxycarbonyl)amino]pentyl-phthalimide (21.5 g) in ethanol is added hydrazine hydrate (20 ml) and the mixture is heated and stirred at 80 ° C. for four hours. The crystal precipitated is filtered and the filtrate is concentrated under reduced pressure to yield 5-(N-tert.-butoxycarbonyl)amino-1-aminopentane (11.9 g) in the colorless oily form.

Elemental analysis for $C_{10}H_{22}N_2O_2$ Calcd. C: 59.37; H: 10.96; N: 13.85. Found C: 59.10; H: 10.71; N: 13.79.

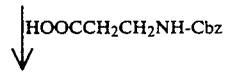

To a solution (20 ml) of 5-(N-tert.-butoxycarbonyl)amino-1-aminopentane (4.0 g) and N-benzyloxycarbonyl-$\beta$-alanine (4.42 g) in N,N-dimethylformamide are added N-hydroxybenztriazole (2.68 g) and dicyclohexylcarbodiimide (4.09 g). The mixture is stirred at room temperature for 20 hours. The insoluble matter is removed by filtration and water is added to the filtrate. The resulting product is extracted with dichloromethane. The dichloromethane layer is washed with water and dried over anhydrous magnesium sulfate. The solvent is distilled off and the crude crystal is recrystallized from ether to yield 1-(N-tert.butoxycarbonyl)amino-5-

(3-N-benzyloxycarbonylaminopropionyl)aminopentane (3.50 g) in a colorless needle form.

Melting point 66°–67 °C.

Elemental analysis for $C_{21}H_{33}N_3O_5$ Calcd. C: 62.98; H: 7.93; N: 10.02. Found C: 62.76; H: 8.15; N: 9.84.

Boc-NH(CH$_2$)$_5$NHCO(CH$_2$)$_2$NH-Cbz    (v)

1. CF$_3$COOH
2. HCl
↓

HCl.H$_2$N(CH$_2$)$_5$NHCO(CH$_2$)$_2$NH-Cbz

A solution (20 ml) of 1-(N-tert.-butoxycarbonyl)amino-5-(3-N-benzyloxycarbonylaminopropionyl)aminopentane (3.50 g) in trifluoroacetic acid is stirred at room temperature for 10 minutes. Then, trifluoroacetic acid is distilled off and 3.6 N hydrochloric acid-dioxane mixture (3 ml) is added thereto. Dioxane is distilled off and the residue is digested with ether to yield 1-(3-N-benzyloxycarbonylaminopropionyl)amino-5-aminopentane hydrochloride (2.77 g) in the powder form.

Melting point 106°–109 °C.

Elemental analysis for $C_{16}H_{25}N_3O_3.HCl$ Calcd. C: 55.88; H: 7.62; N: 12.22. Found C: 55.95; H: 7.83; N: 12.08.

HCl.H$_2$N(CH$_2$)$_5$NHCO(CH$_2$)$_2$NH-Cbz    (vi)

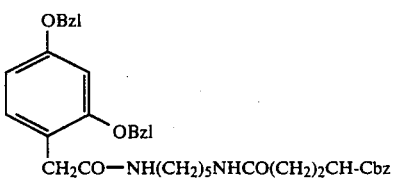

To solution (10 ml) of 1-(3-N-benzyloxycarbonylaminopropionyl)amino-5-aminopentane hydrochloride (515 mg) and 2,4-dibenzyloxyphenylacetic acid (252 mg) in N,N-dimethylformamide are added triethylamine (0.21 ml), N-hydroxybenztriazole (203 mg) and dicyclohexylcarbodiimide (330 mg), in this order and the mixture is stirred at room temperature for eight hours. Water is added to the reaction solution and the product is extracted with dichloromethane. The dichloromethane layer is washed with water and dried over anhydrous magnesium sulfate. The solvent is distilled off to obtain a glass-like product. This is digested with ether into powder. The product is filtered and dried to yield 1-(2,4-dibenzyloxyphenylacetyl)-amino-5-(3-benzyloxycarbonylaminopropionyl)aminopentane (0.50 g).

Elemental analysis for $C_{38}H_{43}N_3O_6$: Calcd. C: 71.56; H: 6.80; N: 6.59. Found C 71.32; H: 6.45; N: 6.37.

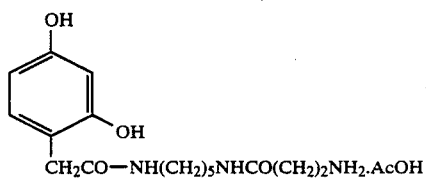

To a solution (20 ml) of 1-(2,4-dibenzyloxyphenylacetyl)amino-5-(3-benzyloxycarbonylaminopropionyl)aminopentane (440 mg) in ethanol are added 10 % palladiumcarbon (70 mg) and acetic acid (0.01 ml) and catalytic reduction is conducted in a hydrogen stream at room temperature under atmospheric pressure. After four hours, the catalyst is removed by filtration and the filtrate is concentrated under reduced pressure. To the glass-like product obtained is added ether to digest into powder. The resulting product is filtered and dried to yield 1-(2,4-dihydroxyphenylacetyl)amino-5-(3-aminopropionyl)aminopentane acetate (209 mg).

SIMS Mass: m/z=324 [M$^+$+H$^+$] $C_{16}H_{25}N_3O_4$: M=323)

Elemental analysis for $C_{16}H_{25}N_3O_4.AcOH.2H_2O$. Calcd. C: 51.54; H: 7.93; N: 10.02. Found C: 51.73; H: 8.19; N: 10.17.

EXAMPLE 14

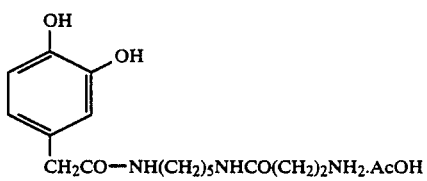

1-(3,4-Dihydroxyphenylacetyl)amino-5-(3-aminopropionyl)aminopentane acetate.

Condensation between 1-(3-N-benzyloxycarbonylaminopropionyl)amino-5-aminopentane hydrochloride (632 mg) and 3,4-dibenzyloxyphenylacetic acid (310 mg) and catalytic reduction for deprotection are carried out in the same manner as in vi) and vii) of Example 13 to yield 1-(3,4-dihydroxyphenylacetyl)amino-5-(3-aminopropionyl)aminopentane acetate (297 mg) in the powder form.

SIMS Mass : m/z=324[M$^+$+H$^+$] (C16H : M =323)

Elemental analysis for $C_{16}H_{25}N_3O_4.AcOH.H_2O$. Calcd. C 56.38; H: 7.62; N: 10.96. Found C: 56.11; H: 7.80; N: 10.75.

EXAMPLE 15

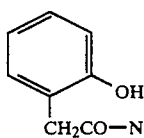

CH₂CO—NH(CH₂)₅NHCO(CH₂)₂NH₂

1-(2-Hydroxylphenylacetyl)amino-5-(3-aminopropionyl)aminopentane

Condensation between 1-(3-N-benzyloxycarbonyl-aminopropionyl)amino-5-aminopentane hydrochloride (516 mg) and 2-hydroxyphenylacetic acid (228 mg) is carried out in the same manner as in Example 13, (vi) and then catalytic reduction for deprotection in the same manner as in Example 13, (vii) to yield 1-(2-hydroxyphenylacetyl)amino-5-(3-aminopropionyl)aminopentane in colorless needle-like crystal (270 mg).

Melting point: 82°–85 ° C.
Elemental analysis for $C_{16}H_{25}N_3O_3$: Calcd: C: 62.52; H: 8.20; N: 13.67. Found C: 62.64; H: 8.19; N: 13.39.

EXAMPLE 16

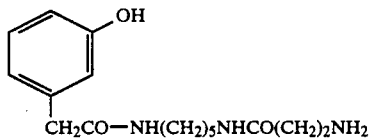

CH₂CO—NH(CH₂)₅NHCO(CH₂)₂NH₂

1-(3-Hydroxyphenylacetyl)amino-5-(3-aminopropionyl)aminopentane

Condensation between 1-(3-N-benzyloxycarbonylaminopropionyl)amino-5-aminopentane and 3-hydroxyphenylacetic acid and then a step for deprotection are carried out in the same manner as in Example 15, thereby colorless needle-like 1-(3-hydroxyphenylacetyl)amino-5-(3-aminopropionyl)aminopentane (300 mg) is obtained.

Melting point 109°–115 ° C.
Elemental analysis for $C_{16}H_{25}N_3O_3$: Calcd. C: 62.52; H: 8.20; N: 13.67. Found C: 62.54; H: 8.49; N: 13.55.

EXAMPLE 17

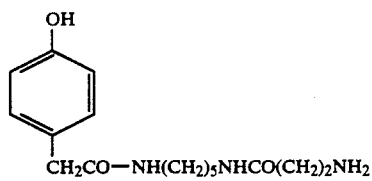

CH₂CO—NH(CH₂)₅NHCO(CH₂)₂NH₂

1-(4-Hydroxyphenylacetyl)amino-5-(3-aminopropionyl)-aminopentane

Condensation between 1-(3-N-benzyloxycarbonyl-aminopropionyl)amino-5-aminopentane and 4-hydroxyphenylacetic acid is carried out in the same manner as in Example 15 to yield colorless needle-like 1-(4-hydroxyphenylacetyl) amino-5-(3-aminopropionyl)aminopentane (0.37 g).

Melting point 180°–183 ° C.
Elemental analysis for $C_{16}H_{25}N_3O_3$: Calcd. C: 62.52; H: 8.20; N: 13.67. Found C: 62.40; H: 8.09; N: 13.73.

EXAMPLE 18

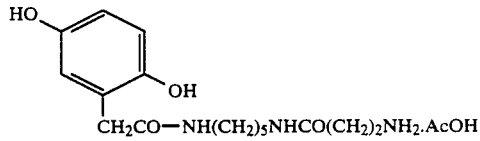

CH₂CO—NH(CH₂)₅NHCO(CH₂)₂NH₂·AcOH

1-(2,5-Dihydroxyphenylacetyl)amino-5-(3-aminopropionyl)-aminopentane acetate Condensation between 1-(3-N-benzyloxycarbonylamino-propionyl)amino-5-aminopentane hydrochloride and 2,5-(dihydroxyphenylacetic acid and then catalytic reduction for deprotection are carried out in the same manner as in Example 13, vi)to yield 1-(2,5-dihydroxyphenylacetyl)amino-5-(3-aminopropionyl)-aminopentane acetate (0.56 g) (glass-like powder).

SIMS Mass : m/z=324[M⁺+H⁺] ($C_{16}H_{25}N_3O_4$: M =323).

Elemental analysis for $C_{16}H_{25}N_3O_4 \cdot AcOH$: Calcd. C: 56.38; H: 7.62; N: 10.96. Found C: 56.11; H: 7.60; N: 10.59.

EXAMPLE 19

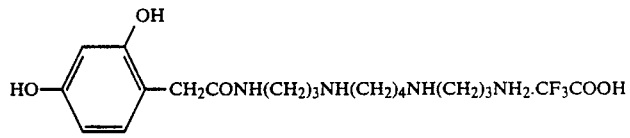

CH₂CONH(CH₂)₃NH(CH₂)₄NH(CH₂)₃NH₂·CF₃COOH

2,4-Dihydroxyphenylacetylspermine trifluoroacetic acid salt

1) To solution of 2,4-dibenzyloxyphenylacetic acid (2.0 g) and para-nitrophenol (920 mg) in N,N-dimethylformamide anhydride (20 ml) is added drop by drop a solution of of dicyclohexylcarbodiimide (1.2 g) in N,N-dimethylformamide anhydride (10 ml) at 0 ° C. and the mixture is left to stand at room temperature (15 ° C.) for 22 hours. The resulting solution is concentrated under reduced pressure to dryness and thereto is added ethyl acetate (70 ml). The precipitate produced is removed by filtration. The filtrate is concentrated under reduced pressure and the residue is separated and purified by use of a silica gel column [silica gel: 350 ml ; developer : hexane-ethyl acetate mixture (4:1)] to yield para-nitrophenyl 2,4-dibenzyloxyphenylacetate (0.70 g; yield 26%).

2) To a solution of spermine (1,4-bis [{(3-amino) propyl}amino]butane, 460 mg) in N,N-dimethylformamide anhydride (5 ml) is added a solution of para-nitrophenyl 2,4-dibenzyloxyphenylacetate (100 mg) in N,N-dimethylformamide anhydride (5 ml). The resulting solution is concentrated to dryness under reduced pressure and thereto are added 5 % aqueous sodium hydrogencarbonate solution (0.1 ml) and then water (30 ml). The resulting precipitate is filtered and washed thoroughly with water, followed by drying, to yield crude 2,4-dibenzyloxyphenylacetylspermine (72 mg, yield 64%).

3) To a solution of crude 2,4-dibenzyloxyphenylacetylspermine (72 mg) in acetic acid (5 ml) is added 10% palladium-carbon (50 mg) and then catalytic reduction is carried out in a hydrogen stream for one and half hours. After the reaction is over, the catalyst is removed by filtration and the filtrate is concentrated to dryness under reduced pressure. The residue is subjected to separation and purification by high-performance liquid chromatography (reversed-phase partition column TSK gel ODS-120T manufactured by Toyo Soda Mfg., CO., Ltd.; inner diameter of the column: 7.8 mm, length: 30 mm; resin diameter; 3 μm; column temperature: 40° C.; eluent: water/acetonitrile mixed solvent (98/2, V/V) to which trifluoroacetic acid has been added to final concentration of 0.05% by volume). The solvent is distilled off to yield 2,4-dihydroxyphenylacetyl-spermine trifluoroacetic acid salt (3.0 mg, yield 4.2%).

Proton NMR of 2,4-dihydroxyphenylacetylspermine trifluoroacetic acid salt (400 MHz, D$_2$O, ppm): 1.54(quin.,4H), 1.70(quin.,2H), 1.90(quin.,2H), 2.83(t,4H), 2.87(t,2H), 2.94(q,4H), 3.15(t,2H), 3.34(s,2H), 6.30(s-like,2H), 6.93(m,1H)

We claim:

1. A compound of the formula:

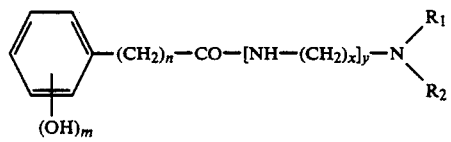

(OH)$_m$ wherein R$_1$ and R$_2$ each is hydrogen atom, an alkyl group optionally substituted with a halogen, hydroxyl, amino, or oxo group or an acyl group optionally substituted with a halogen, hydroxyl, amino, or oxo group or

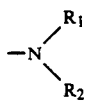

is a cyclic amino group formed by elimination of a hydrogen atom from NH in 5- to 24- membered cyclic amine represented by

HNR in which ring constituting atoms are C, N, O, S, or combination thereof optionally substituted on N with a lower alkyl group, an aryl group, an aralkyl group, or an acyl group and optionally substituted on C with a lower alkyl group, an acyl group, a lower alkylidene group, an oxo group, or a thioxo group, m is 2 such that the positions of the OH group are 2,4- or 3,4- on the benzene ring, n is an integer of 0 to 4, x is an integer of 2 to 6 and y is an integer of 0 to 3, or a salt thereof.

2. A compound as claimed in claim 1, wherein both R$_1$ and R$_2$ are hydrogen atoms.

3. A compound as claimed in claim 1, wherein

is a cyclic amino group formed by elimination of a hydrogen atom from NH in a 5- to 24-membered cyclic amine represented by

HNR in which ring constituting atoms are C, N, O, S, or combination thereof optionally substituted on N with a lower alkyl group, an aryl group, an aralkyl group, or an acyl group and optionally substituted on C with a lower alkyl group, an acyl group, a lower alkylidene group, an oxo group, or a thioxo group.

4. A compound as claimed in claim 1, which is 1-(2,4-dihydroxyphenylacetyl)-4-(4-fluorobenzoyl)piperidene.

5. A compound as claimed in claim 1, which is 1-(2,4-dihydoxyphenylacetyl)-4-benzylpiperidine.

6. A compound as claimed in claim 1, which is 1-(2,4-dihydroxyphenylacetyl)-4-benzylpiperazine.

7. A compound as claimed in claim 1, which is 1-(2,4-dihydroxyphenylacetyl)amino-5-(3-aminopropionyl)aminopentane.

8. The use of a compound as defined in claim 1, or a pharmaceutically acceptable salt thereof for the prevention of the sequelae of cerebral apoplexy in a warm-blooded animal comprising administering to the animal an effective amount of the compound.

* * * * *